United States Patent
Burry et al.

(10) Patent No.: US 6,632,422 B2
(45) Date of Patent: Oct. 14, 2003

(54) ANTIPERSPIRANT AND DEODORANT PRODUCTS AND METHODS FOR THEIR USE

(75) Inventors: Jason Shaun Burry, Bebington (GB); Richard Livesey Evans, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/920,779

(22) Filed: Aug. 2, 2001

(65) Prior Publication Data

US 2002/0037264 A1 Mar. 28, 2002

(30) Foreign Application Priority Data

Aug. 3, 2000 (GB) .............................................. 0019055

(51) Int. Cl.[7] ............................. A61K 7/32; A61K 7/38; A61K 7/00; A61K 35/78
(52) U.S. Cl. ........................... 424/65; 424/68; 424/401; 424/746
(58) Field of Search ......................... 424/65, 68, 401, 424/746

(56) References Cited

U.S. PATENT DOCUMENTS

| | | | |
|---|---|---|---|
| 3,312,709 A | 4/1967 | MacMillian | 260/292 |
| 4,022,787 A | 5/1977 | Soldati et al. | 260/293.81 |
| 4,517,176 A | 5/1985 | Felger | 424/47 |
| 4,546,096 A | 10/1985 | Herlihy et al. | 514/25 |
| 4,720,494 A | 1/1988 | Felger et al. | 514/252 |
| 4,797,410 A * | 1/1989 | El-Fakahany | |
| 6,139,825 A | 10/2000 | Reinhard et al. | 424/65 |

FOREIGN PATENT DOCUMENTS

| | | |
|---|---|---|
| CN | 1107061 * | 8/1995 |
| DE | 195 41 735 | 5/1997 |
| EP | 1 064 932 | 1/2001 |

OTHER PUBLICATIONS

Choi, E.H. et al. SKin Pharmacol. Appl. Skin Physiol., 1999, 12:326–335.*
PCT Search Report in a PCT application PCT/EP 01/08702.
Derwent Abstract of XP–002096995—published Nov. 30, 1985.
Derwent Abstract of JP 05 331021—published Dec. 14, 1993.
Derwent Abstract of JP 01 129854—published May 23, 1989.
Chemical Abstracts, vol. 126, No. 4, "Anion secretion induced by capacitative Ca2+ entry through apical and basolateral membranes of cultured equine sweat gland epithelium"—published Jan. 27, 1997.
Chemical Abstracts, vol. 127, No. 2, "Preparation of (substituted)allylbenzenes by molybdenum or tungsten–catalyzed reaction of benzenes with allyl compounds"—published Jul. 14, 1997.
Chemical Abstracts, vol. 137, No. 26, "Plant–based materials containing chemicals for vaporization"—published Jun. 26, 2000.
Chemical Abstract of EP 1 064 932—published Jan. 3, 2001.
Derwent Abstract of DE 195 41 735—published May 15, 1997.
GB Search Report in GB application GB 0019055.3.
J. Biological Chem., 1988, 263, 2238–2244, V.F. King et al., "Internaction of tetrandrine with slowly inactivating calcium channels".
Arch Dermatol., 1987, 123, 925–929, WD James et al., "Emotional eccrine sweating".
Derwent Abstract of CN 1117868, published Mar. 6, 1996.
Derwent Abstract of CN 1135346, published Nov. 13, 1996.
Derwent Abstract of JP 62–221619, published Sep. 29, 1987.
Derwent Abstract of CN 1107061, published Aug. 23, 1995.
Derwent Abstract of RU 2045263, published Oct. 10, 1995.

* cited by examiner

Primary Examiner—Christopher R. Tate
Assistant Examiner—Kailash C. Srivastava
(74) Attorney, Agent, or Firm—Kevin J. Stein

(57) ABSTRACT

A new method for the inhibition of human sweating and body malodour is described. An agent capable of blocking calcium channels in the secretory coil cells of human sweat glands is topically applied; on reaching the secretory coil cells, the action of this agent results in reduced sweat production. Preferred agents are natural plant extracts. The transport of the agent to the secretory coil is preferably enhanced in some way, for example by iontophoresis or the use of a skin penetration enhancer. Antiperspirant products comprising a calcium channel blocking agent and a pore-blocking antiperspirant active are also claimed.

10 Claims, No Drawings

ANTIPERSPIRANT AND DEODORANT PRODUCTS AND METHODS FOR THEIR USE

FIELD OF INVENTION

This invention relates to antiperspirant and deodorant products and to cosmetic methods of reducing perspiration and unpleasant body odours.

BACKGROUND OF INVENTION

Cosmetic antiperspirant and deodorant compositions are known. Typical antiperspirant compositions comprise topically acceptable compositions containing a metal salt, such as an astringent aluminium or aluminium/zirconium salt, in combination with a cosmetically suitable vehicle. Typical deodorant compositions comprise topically acceptable compositions containing one or more agents that mask or inhibit the formation of unpleasant body odours; antimicrobial agents are widely used for this purpose. Such cosmetic antiperspirant and deodorant products may be available in a variety of product forms, for example as sticks, roll-on lotions, aerosols and pump spray formulations.

Whilst such compositions provide a degree of malodour reduction, there are problems associated with their use. For example, some people find that such compositions are insufficiently effective. Others find that the application of astringent antiperspirant salts or certain anti-microbial agents leads to skin irritation. Other problems include formulation difficulties with the high levels of active ingredients sometimes required. It has long been desirable to achieve excellent protection from body malodour without the use of high concentrations of conventional antiperspirant or deodorant agents. This could lead to antiperspirant and deodorant products being cheaper, easier to formulate (by virtue of the reduced amount of antiperspirant active used), or generally having improved sensory properties. Other benefits of requiring lesser amounts of conventional antiperspirant or deodorant agents include the reduced concentration on the body of such 'foreign' agents and the reduced impact on the environment, in terms of chemical usage and processing.

The use of numerous "non-conventional" antiperspirant or deodorant agents are described in the prior art. For example, the use of anticholinergic materials is described in U.S. Pat. No. 3,312,709 (MacMillan, 1967); U.S. Pat. No. 4,022,787 (Soldati et al, 1977); and a series of patents by Felger et al (U.S. Pat. No. 4,517,176, 1985; U.S. Pat. No. 4,546,096, 1988; U.S. Pat. No. 4,720,494, 1988). Such materials are claimed to reduce perspiration at source, that is to say at the secretory coil of the sweat glands.

The present invention is concerned with materials that can be termed "calcium channel blocking agents" ("CCBA"s, vide infra). One such material, methoxy-verapamil, has been shown, in vitro, to reduce sweat production from isolated cannulated monkey palm eccrine sweat glands (Sato and Sato, *Am. J. Physiol.*, 1981, 241, C113–C120). Other CCBAs have been demonstrated to be physiologically active in various types of tissue; for example, tetrandrine, an alkaloid isolated from the root of Stephania tetrandra, has been shown to be capable of inhibiting calcium influx into the aortic smooth muscle cells of rats (Wu et al, *Eur. J. Pharmacol.*, 1997, 327, 233–238) and *Panax ginseng* root extract has been shown to inhibit calcium channels in rat sensory neurons (Nah and McCleskey, *J. Ethnopharmacol.*, 1994, 42, 45–51). In another application, all CCBAs, together with substances that reduce the binding of calcium to intracellular proteins, are claimed to relax and/or loosen cutaneous and/or subcutaneous tissue (EP 1,053,745, 2000).

Plant extracts that may comprise CCBAs are described as components in various cosmetic or pharmaceutical preparations. For example, Chinese patent application CN 1117868A claims a Chinese medicine with ginseng that cures night sweating; CN 1135346A claims medicinal compositions with ginseng that induce sweating and JP 62221619A claims that *Panax ginseng* promotes perspiration; CN 1107061A claims that *Stephania tetrandra* deodorises and stops sweating and Russian patent RU 2045263 claims body antiperspirants comprising ginseng extract.

SUMMARY OF INVENTION

According to a first aspect of the present invention, there is provided use of a calcium channel blocking agent (CCBA) in a cosmetic product, or in the preparation of a cosmetic product, intended for the reduction of perspiration and/or body malodour, characterised in that said CCBA is of molecular weight less than 750.

According to a second aspect of the present invention, there is provided a cosmetic method of reducing underarm perspiration, said method comprising topical application to the underarm area of a cosmetic product comprising a CCBA of molecular weight less than 750.

According to a third aspect of the present invention, there is provided a cosmetic product comprising a CCBA of molecular weight less than 750 and an anti-microbial agent, characterised in that said anti-microbial agent has an MIC of 1 $mg.ml^{-1}$ or less.

According to a fourth aspect of the present invention, there is provided a cosmetic product comprising a CCBA, characterised in that said product comprises an additional agent that enhances the perceived antiperspirancy benefit.

According to a fifth aspect of the present invention, there is provided a cosmetic method of obtaining an antiperspirancy benefit, comprising the topical application of a cosmetic product according to the aforementioned fourth aspect of the invention.

DETAILED DESCRIPTION OF THE INVENTION

The method of reducing sweat production described herein represents a major step forward in the cosmetic treatment of sweating and body malodour. We have discovered that it is possible to reduce, or even prevent, sweat production from human sweat glands by topical administration of cosmetic products according to the invention. The invention is of greatest benefit when used in the treatment of the more sweaty areas of the body, in particular the underarm areas and, in some embodiments, the feet.

It is believed that the CCBA serves to reduce sweat production at source, that it to say, the CCBA reduces secretion of primary sweat from the secretory coil cells of the sweat glands. Sweat production is triggered by either cholinergic or adrenergic stimulation of the cells of the secretory coil. In response to this stimulation, there is an increase in the intracellular calcium concentration, which in turn initiates a cascade of events resulting in the production of primary sweat. The required elevated level of calcium within the cells of the secretory coil is sustained by an influx of calcium into the cells via calcium channels in the basolateral and/or apical cell membrane. By blocking these calcium channels production of sweat can be reduced or even prevented.

The eccrine sweat glands are the preferred target for the prevention of sweating, these being involved in the body's thermoregulatory responses as well as emotional responses. Prevention of sweat production from the apocrine secretory coil cells offers benefits when sweat stimulation is brought about by pain or an emotive trigger, for example nervousness. For optimum protection from sweat production, whatever the cause, it is preferred that the CCBA acts upon both the eccrine and apocrine secretory coil cells.

This new method of sweat reduction can be used to augment or replace methods involving the use of pore-blocking antiperpirant actives. When used to augment the use of such actives, the cosmetic product used comprises a CCBA and a pore-blocking antiperpirant active. Such pore-blocking antiperspirant actives include astringent metal salts of the type described hereinafter. Typically, the CCBA employed in such products has a molecular weight less than 750.

The present invention involves topical application of the CCBA, which must penetrate through the skin and reach the secretory coil cells of the sweat glands in sufficient concentration to be effective. Transport of the CCBA from the skin surface to the secretory coil cells may be enhanced in a number of ways.

In one embodiment of the present invention, the transport of the CCBA is enhanced by iontophoresis. Iontophoresis is a method of aiding the passage of polar molecules into the skin by applying a small electrical current. A low voltage (usually from a battery) is applied to a solution of the CCBA in contact with the subject's skin. The voltage serves to drive charged ions through the skin, thereby delivering the CCBA, in charged form.

In a preferred embodiment of the invention, the transport of the CCBA is enhanced by the presence of a skin penetration enhancer (SPE) that helps the CCBA to penetrate the skin.

In cosmetic products comprising a CCBA and a pore-blocking antiperspirant active and/or an SPE, it is not essential that these components are part of the same composition. The antiperspirancy benefit derived from use of the invention may be gained by independent application of the components. Such application may be concurrent or consecutive, provided that the body experiences the presence of the components at the same time. When the components are applied from independent compositions, it is preferred that the product also comprises a means for, and/or instruction for, each of the compositions to be applied to the body.

For convenience, it is preferred that the components are present in the same composition.

Other components are also desirably present, particular examples including anti-microbial agents, and/or a carrier material, and/or a transition metal chelator (vide infra).

Calcium Channel Blocking Agent (CCBA)

The CCBAs of the present invention may block any of the calcium channels that exist in the basolateral and/or apical cell membrane. Such calcium channels may be classified as being either voltage-dependent or voltage-independent. The former group is operated by changes in membrane potential and includes six types of channel (L, N, T, P Q, and R). Detailed information on voltage dependent channels and the agents that block them is given by Glossmann and Streissnig in *Rev. Phys. Biochem. Pharmacol.*, 1990, 114, 1–105. Voltage-independent channels are either operated by membrane receptors or by the depletion of calcium stores in the cytoplasm (store operated channels [SOCs]). Detailed information on voltage independent channels and the agents that block them is given by Clementi and Meldolesi in *Cell Calcium*, 1996, 19(4), 269–279. Of the SOCs, the transient receptor potential (TRP) family is particularly well characterised (see Harteneck, Plant, and Schultz, *Trends in Neurosciences*, 2000, 23(4), 159–166).

Examples of CCBAs include those mentioned in the three publications referred to in the above paragraph and those mentioned in EP 1,053,745, 2000. Particular examples include phenylalkylamines, such as D600 (methoxy-verapamil), verapamil, desmethoxy-verapamil, anipamil, gallopamil, devapamil, falipamil, and tiapamil; dihydropyridines, such as nifedipine, amlodipine, dazodipine, felodipine, isradipine, lanicarpidine, nimodipine, nisoldipine, nitrendipine, and ryosidine; benzothiazepines, such as diltiazem; and diphenylpiperazines, such as cinnarizine and flunarizine; toxins, such as apamin; 2-aminoethoxydiphenyl berate; SDZ-202 791 R(-), from Sandoz; and SK&F 96365, Smith, Kline, and French.

Our studies have shown, for the first time, that CCBAs have the ability to reduce calcium influx into the secretory coil cells of human eccrine or apocrine glands. The following procedure, or one essentially the same, may be used to test a material for this ability.

The procedure is performed on an isolated human sweat gland. Collapsed segments of secretory coil are held between two glass pipettes in the perfusion bath of an inverted microscope and bathed at 37° C. in a solution buffered to pH 7.4. Intracellular calcium may be measured by any convenient means; in our tests the fluorescent dye FURA-2 AM was used (full details are given in Examples 1 and 2). The calcium influx induced by the administration of methylcholine at 1 $\mu$mol.dm$^{-3}$ is compared before and after the introduction of the test material into the buffer solution. Test materials are classed as CCBAs if they are able to reduce the methylcholine-induced calcium influx into the cells, preferably by at least 20%, more preferably by at least 50%. The concentration of test material used should be between 1 and 100 $\mu$mol.dm$^{-3}$ for pure compounds, 25 $\mu$mol.dm$^{-3}$ being a typical concentration of use. When the test material used is not a pure compound, for example when it is a plant extract, allowance must be made for the non-active components in the extract when choosing the test dosage.

Blocking of voltage dependent calcium channels, in particular L-type calcium channels, is believed to be particularly valuable in reducing sweat production from the secretory coil of human sweat glands. Hence, voltage dependent CCBAs, in particular L-type CCBAS, are preferred in all aspects of the present invention. Especially preferred L-type CCBAs are verapamil (including salts thereof) and methoxy-verapamil (including salts thereof). Other preferred CCBAs are cosmetic ingredients, especially those included in the database of the Cosmetic Toiletries and Fragrance Association. Particularly preferred agents are present in plant extracts, for example those derived from Stephania sp., in particular *Stephania tetrandra;* Salvia sp., in particular Red Sage (*Salvia miltiorrhiza*); Magnolia sp., in particular *Magnolia offinalis* and *Magnolia fargesii;* and Astragalus sp., in particular Milk vetch (*Astragalus membranaceus*). The active components in these extracts are all natural ingredients and such ingredients are particularly preferred. An especially preferred agent is Safrole, which is present in many natural extracts, including those obtained from *Sassafras albidum, Myristica frangrans,* and *Ocimum basilicium.* Other especially preferred agents present in natural extracts are tanshinone (ex Red Sage), magnolol (ex *Magnolia officinalis*), and denudin B, (ex *Magnolia fargesii*).

The transport of the CCBA from the skin surface to the secretory coil cells of the sweat glands is aided by the CCBA being of relatively low molecular weight. In certain aspects of the invention, it is essential that the CCBA has a molecular weight of less than 750. In all aspects of the invention, it is preferred that the CCBA has a molecular weight of less than 650, in particular less than 600. In general, the molecular weight will be above 100 and usually above 150. Skin penetration is also aided by the CCBA having a moderate to high hydrophobicity, that is to say having a c.logP of between −1 and 5, where c.logP is the logarithm to the base 10 of the calculated octanol/water partition coefficient. By way of example, verapamil has a c.logP of 4.47 and nifedipine has a c.logP of 3.42.

It is highly preferred that the CCBA employed is of low irritancy. Such materials, when applied as a 0.1% solution by weight in a suitable solvent, have an erythema grading of less than 5, in particular less than 4, and especially less than 3, as assessed by the method described by Basketter et al in *Contact Dermatitis*, 1997, 37, 218–220. For this reason and/or others it is preferred that the CCBA does not possess any strongly acidic functional groups (eg. sulphonic acid groups) or any phenolic functional groups.

Mixtures of CCBAs may be employed and references to preferred amounts of CCBA refer to the total amount of all CCBAs present. This statement also applies, mutatis mutandis, to the other components that may be present.

It is preferred that the CCBA be used at a concentration sufficient to deliver at least 1 $\mu$mol.dm$^{-3}$ to the environs of the secretory coil cells. More preferably the level delivered is from 1 to 1000 $\mu$mol.dm$^{-3}$, especially from 10 to 1000 $\mu$mol.dm$^{-3}$, and most especially from 10 to 100 $\mu$mol.dm$^{-3}$. The level required in a cosmetic composition for topical administration is approximately 10 to 5000 times these concentrations, due to dilution on permeation through the skin. Hence, embodiments of the invention preferably involve cosmetic compositions comprising approximately from 0.1 to 250 mmol.kg$^{-1}$ of CCBA. With suitable delivery enhancement present, for example in compositions also comprising an SPE, the amount of CCBA required may be somewhat less, preferred levels being 0.1 to 100 mmol.kg$^{-1}$, more preferably 0.1 to 50 mmol.kg$^{-1}$.

Additional Components

A pore-blocking antiperspirant active is a desirable component in certain embodiments of the invention. Such materials include astringent metal salts conventionally used as antiperspirant salts. Examples include aluminium, zirconium and mixed aluminium/ zirconium salts, including both inorganic salts, salts with organic anions and complexes. Preferred astringent salts include aluminium, zirconium and aluminium/zirconium halides and halohydrate salts, such as chlorohydrates. When included, preferred levels of incorporation are from 0.5% to 60%, particularly from 5% to 30% or 40% and especially from 5% or 10% to 30% or 35% by weight of the composition. Especially preferred aluminium halohydrate salts, known as activated aluminium chlorohydrates, are described in EP 6,739 (Unilever PLC and NV). Zirconium aluminium chlorohydrate actives are also preferred materials, as are the so-called ZAG (zirconium-aluminium-glycine) complexes, for example those disclosed in U.S. Pat. No. 3,792,068 (Procter and Gamble Co.).

An additional component that can sometimes augment the ability of the compositions of the invention to reduce body odour is an anti-microbial agent. Most of the classes of agents commonly used in the art can be incorporated into compositions of the invention. Levels of incorporation are preferably from 0.01% to 3%, more preferably from 0.03% to 0.5% by weight of the non-volatile components of the composition.

In the context of this invention, a non-volatile component is one having a boiling point of at least 50° C., at atmospheric pressure.

Preferred compositions of the invention comprise an anti-microbial agent having a minimum inhibitory concentration (MIC) of 1 mg.ml$^{-1}$ or less, particularly 200 $\mu$g.ml$^{-1}$ or less, and especially 100 $\mu$g.ml$^{-1}$ or less. The MIC of an anti-microbial agent is the minimum concentration of the agent required to significantly inhibit microbial growth. Inhibition is considered significant if an 80% or greater reduction in the growth of an inoculum of a relevant micro-organism is observed, relative to a control medium without an anti-microbial agent, over a period of 16 to 24 hours at 37° C. A relevant micro-organism that may be used is *Staphylococcus epidermidis*. Details of suitable methods for determining MICs can be found in "Antimicrobial Agents and Susceptibility Testing" C. Thornsberry, (in "Manual of Clinical Microbiology", 5$^{th}$ Edition, Ed. A. Balows et al, American Society for Microbiology, Washington D.C., 1991). A particularly suitable method is the Macrobroth Dilution Method, as described in Chapter 110 of above publication (pp. 1101–1111) by D. F. Sahm and J. A. Washington II. MICs of anti-microbials suitable for inclusion in the compositions of the invention are triclosan: 0.01–10 $\mu$g.ml$^{-1}$ (J. Regos et al., Dermatologica (1979), 158: 72–79) and farnesol: ca. 25 $\mu$g.ml$^{-1}$ (K. Sawano, T. Sato, and R. Hattori, Proceedings of the 17$^{th}$ IFSCC International Conference, Yokahama (1992) p.210–232). By contrast ethanol and similar alkanols have MICs of greater than 1 mg.ml$^{-1}$. Preferred anti-microbials are bactericides, in particular organic bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred anti-microbials are bactericides having an MBC (minimum bactericidal concentration) of 1 mg.ml$^{-1}$ or less, particularly 200 $\mu$g.ml$^{-1}$ or less, and especially 100 $\mu$g.ml$^{-1}$ or less. Examples of preferred anti-microbials are polyhexamethylene biguanide salts (also known as polyaminopropyl biguanide salts), an example being Cosmocil CQ available from Zeneca PLC, preferably used at up to 1% and more preferably at 0.03% to 0.3% by weight; 2',4,4'-trichloro, 2-hydroxy-diphenyl ether (triclosan), preferably used at up to 1% by weight and more preferably at 0.05–0.3% by weight of the non-volatile components of the composition; and 3,7,11-trimethyldodeca-2,6,10-trienol(farnesol), preferably used at up to 1% and more preferably at up to 0.5% by weight of the non-volatile components of the composition.

Inorganic anti-microbial agents may also be employed, for example zinc phenol sulphonate, preferably at up to 3% by weight of the non-volatile components of the composition.

Skin penetration enhancers (SPEs) are desirable components in certain embodiments of the invention. Such materials are capable of aiding the transport of the CCBA from the skin surface to the eccrine and/or apocrine secretory coil cells. It is highly preferably that such materials are co-soluble with the CCBA employed. Generally, the SPE can be a solvent for the CCBA, the CCBA preferably having a solubility in the SPE of greater than 50 mmol.dm$^{-3}$, more preferably greater than 100 mmol.dm. Suitable SPEs include oleic acid, azone, urea, transcutol, and ethanol. Preferred SPEs are short chain polyhydric alcohols, in particular C2 to C5 alcohols with 2–5 hydroxy groups, especially glycerol and propylene glycol. The SPE may be present at a level of 0.5–90% by weight of the composition in which it is employed, excluding any propellant that may be present. Preferably this level is 1–50% by weight, more preferably from 2–30%, and most preferably from 3–12%.

The ratio of SPE to CCBA in the compositions of the invention is also important. It is preferred that the weight ratio of SPE:CCBA is from 1:1 to 100:1, especially from 2:1 to 50:1, and most especially from 5:1 to 10:1.

A carrier material for the CCBA, is a preferred additional component in the compositions used in the present invention. The carrier material may be hydrophobic or hydrophilic, solid or liquid. Preferred carrier materials are liquids at ambient temperature and atmospheric pressure. Hydrophobic liquids suitable for use include liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, and aliphatic or aromatic ester oils (eg. isopropyl myristate, lauryl myristate, isopropyl palmitate, diisopropyl sebecate, diisopropyl adipate, or $C_8$ to $C_{18}$ alkyl benzoates).

Hydrophilic liquid carrier materials, for example water, may also be employed.

Particularly preferred liquid carrier materials comprise organic solvents. Preferred organic solvents have a melting point of less than 10° C., preferably less than 5° C.; this can benefit both low temperature storage stability and ease of manufacture. A class of preferred organic solvents are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol propylene glycol, butylene glycol, ethanol, propanol, isopropanol, and industrial methylated spirits. The most preferred organic solvents are aliphatic alcohols, in particular those having 2 to 3 carbon atoms, especially ethanol and isopropanol. Especially preferred liquid carrier materials are also able to function as SPEs (vide supra), for example ethanol.

Mixtures of carrier materials may also be used. The total amount of carrier material employed is preferably from 30% to 99%, more preferably 60% to 98%, expressed as a weight percentage of the total weight of the composition of which it is a part, excluding any volatile propellant that may be present.

In certain embodiments of the invention, a transition metal chelator is desirably present. Such materials may enhance deodorancy benefits and/or the perceived antiperspirancy benefit; the latter benefit also being common to pore-blocking antiperspirant actives. Examples of transition metal chelators are described in U.S. Pat. No. 4,356,190 (Personal Products Co.) and our co-pending application PCT/EP01/00118 (Unilever). Often such materials are acids, although they may be used in their acid form or as salts, for the purposes of this invention. Preferred transition metal chelators have an iron (III) binding constant of greater than $10^{26}$; examples including diethylenetriaminepentaacetic acid (DTPA), trans-1,2-diaminocyclohexane-N,N,N',N'-tetraacetic acid (CDTA), and triethylenetetraaminehexaacetic acid (TTHA). Particularly preferred is DTPA. Such agents may be used in concentrations ranging from 0.001 to 10% by weight of the composition, preferably from 0.01 to 3%, excluding any volatile propellant that may also be present in the composition.

Structurants and emulsifiers are further additional components that are highly desirable in certain product forms. Structurants, when employed, are preferably present at from 1% to 30% by weight of the composition of which they are a part, whilst emulsifiers are preferably present at from 0.1% to 10% by weight. In roll-ons, such materials help control the rate at which product is dispensed by the roll ball. In stick compositions, such materials can form gels or solids from solutions or suspensions of the chelator salt in a carrier fluid. Suitable structurants for use in such compositions of the invention include cellulosic thickeners such as hydroxy propyl cellulose and hydroxy ethyl cellulose, and dibenzylidene sorbitol. Emulsion pump sprays, roll-ons, creams, and gel compositions according to the invention can be formed using a range of oils, waxes, and emulsifiers. Suitable emulsifiers include steareth-2, steareth-20, steareth-21, ceteareth-20, glyceryl stearate, cetyl alcohol, cetearyl alcohol, PEG-20 stearate, and dimethicone copolyol. Suspension aerosols, roll-ons, sticks, and creams require structurants to slow sedimentation (in fluid compositions) and to give the desired product consistency to non-fluid compositions. Suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Some of the above materials also function as suspending agents in certain compositions.

Further emulsifiers desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers.

Certain sensory modifiers are further desirable components. Such materials are preferably used at a level of up to 20% by weight of the composition of which they are a part. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (eg. Aerosil 200), polyethylene (eg. Acumist B18), polysaccharides, corn starch, C12–C15 alcohol benzoate, PPG-3 myristyl ether, octyl dodecanol, C7–C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in the compositions of the invention. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight of the composition of which they are a part.

It should be noted that certain components of compositions perform more than one function. Such components are particularly preferred additional ingredients, their use often saving both money and formulation space. Examples of such components include ethanol, isopropyl myristate, and the many components that can act as both structurants and sensory modifiers, for example silica.

Further additional components that may also be included are colourants and preservatives, for example $C_1$–$C_3$ alkyl parabens.

Product Forms

The compositions employed may take any form. Examples include wax-based sticks, soap-based sticks, compressed powder sticks, roll-on suspensions or solutions, emulsions, gels, creams, squeeze sprays, pump sprays, and aerosols. Each product form contains its own selection of additional components, some essential and some optional. The types of components typical for each of the above product forms may be incorporated in the corresponding compositions of the invention. Roll-on compositions particularly suited to the invention are simple solutions in organic solvents, although water can be tolerated in such compositions. In addition, emulsion compositions, for example oil-in-water and water-in-oil emulsions, are not excluded. Stick compositions of the invention are preferably based on either a monohydric or polyhydric alcohol organic solvent base. They are often gelled with sodium stearate, although dibenzylidene sorbitol (DBS) may alternatively be used, preferably in combination with hydroxypropyl cellulose.

Aerosol compositions of the invention may comprise from 30 to 99 parts by weight, and particularly 30 to 60 parts by weight of propellant and the remainder (respectively 70 to 1 and particularly 70 to 40 parts by weight) of the antiperspirant/deodorant base composition.

The propellant in the aerosol compositions may be selected from liquified hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane. Other propellants that can be contemplated include alkyl ethers, such as dimethyl ether or compressed non-reactive gasses such air, nitrogen or carbon dioxide.

Methods of Manufacture

The compositions of the invention may be manufactured by any convenient method. In a particular embodiment of present invention, a suitable composition is manufactured by the addition of a CCBA and an SPE for said CCBA to an appropriate carrier material, the components being agitated to give a homogeneous mixture. Said mixture may be used in any of the product forms described above, with the incorporation of the appropriate additional components.

EXAMPLES

Example 1

This example illustrates the ability of the CCBA tetrandrine (as derived from *Stephania tetrandra*) to reduce calcium influx into the secretory coil cells of human eccrine glands.

Collapsed segments of secretory coil were held between two glass pipettes in the perfusion bath of an inverted Olympus IMT-2 microscope and bathed in a solution at 37° C. containing (in mmol.dm$^{-3}$): sodium chloride, 130; HEPES (buffer; 4-[2-hydroxyethyl]-1-piperazineethanesulphonic acid), 20; potassium chloride, 5; calcium chloride, 1; magnesium chloride, 1; and glucose, 10. The pH of the solution was adjusted to 7.4 using 1 mol.dm$^{-3}$ sodium hydroxide solution.

The calcium influx was induced by the administration of methylcholine (a cholinergic agonist) at 1 μmol.dm$^{-3}$. This was first done for control solutions containing no CCBA and then for test solutions containing tetrandrine (various dosages). The results, illustrated in Table 1 as percentage reductions in calcium influx, show the ability of tetrandrine to function as a highly effective CCBA.

TABLE 1

Inhibition of Methylcholine-induced Calcium Influx into Human Eccrine Secretory Coil Cells

| CCBA | dosage (μmol.dm$^{-3}$ for tetrandrine) | Ca influx inhibition[2] (%) |
|---|---|---|
| Tetrandrine[1] | 100 | 100 |
|  | 50 | 96 |
|  | 25 | 75 |
|  | 10 | 44 |
|  | 1 | 24 |
| None (control) |  | 0 |

[1]S,S (+) enantiomer, ex Aldrich.
[2]See below for measurement technique details. All results significantly different to the control result at the 95% level of significance.

Intracellular calcium concentration was measured using the fluorescent probe Fura-2, a dye that has high affinity for calcium. When illuminated with ultraviolet light at 350 and 380 nm, Fura-2 emits corresponding fluorescent signals. Importantly, when calcium binds to the dye, the magnitude of the emitted fluoresence signal alters. It is these changes that are used to calculate the intracellular calcium concentration (vide infra).

Segments of secretory coil were incubated for 40 minutes, at 37° C., with 5 μm.dm$^{-3}$ Fura-2 AM. This form of Fura-2 is lipid soluble and readily enters the cell where the AM group is cleaved off by esterases, leaving the fluorescent lipid-insoluble dye trapped within the cells. Excitation light at 350 and 380 nm was supplied from a computer controlled Photon Technology International (PTI) spectrofluorimeter. This light was passed through a 390 nm dichroic mirror, prior to passage through the microscope objective (×40) and onto the tissue sample. The fluorescence resulting from the tissue was passed through a 505 nm bandpass filter, before being detected by a photomultiplier tube. The output from the photomultiplier tube was digitised and analysed using Photon Technology International software. Background fluorescence (measured prior to introduction of the Fura-2 AM) was subtracted from the total signal for each wavelength and a value representing the intracellular calcium concentration was obtained by dividing the fluorescence value resulting from the 350 nm excitation light by that resulting from the 380 nm excitation light.

Example 2

This example illustrates the ability of tetrandrine to reduce calcium influx into the secretory coil cells of human apocrine glands.

The same method as described in Example 1 was used, the only procedural changes being the use of 50 μmol.dm$^{-3}$ methylcholine to induce the calcium influx and the use of human apocrine glands, rather than eccrine glands. The results, illustrated in Table 2 as percentage reductions in calcium influx, show the ability of tetrandrine to function as a highly effective CCBA in the secretory coil cells of human apocrine glands.

TABLE 2

Tetrandrine Inhibition of Methylcholine-induced
Calcium Influx into Human Apocrine Secretory Coil Cells

| Tetrandrine[1] dosage ($\mu$mol.dm$^{-3}$) | Ca influx inhibition[2] (%) |
|---|---|
| 50 | 93 |
| 10 | 60 |
| 0 | 0 |

[1]S,S (+) enantiomer, ex Aldrich.
[2]Measurement technique details as before. Both results significantly different to the control result at the 99% level of significance.

These two experiments demonstrate that the CCBA tetrandrine can reduce calcium influx into the secretory coil cells of both human eccrine glands and human apocrine glands, which leads to reduced sweat production at source.

Example 3

This example illustrates the ability of CCBAs to reduce sweat secretion from isolated human eccrine glands.

The method employed was analogous to that described by Sato and Sato in *Am. J. Physiol.*, 1973, 225, 1147–1151.

TABLE 3

In vitro Sweat Reduction Studies

| CCBA | Dosage ($\mu$mol.dm$^{-3}$) | % reduction in sweat secretion |
|---|---|---|
| Tetrandrine[1] | 50 | 93 |
| Verapamil hydrochloride[2] | 1000 | 93 |
| None (control | — | 0 |

[1]S,S (+) enantiomer, ex Aldrich.
[2]ex Sigma.

Example 4

This example illustrates an in vivo sweat reduction benefit on topical application of a cosmetic product comprising a CCBA.

TABLE 4

Compositions Used in In Vivo Study
(amounts are percentages by weight)

| | Test Composition | Control Composition |
|---|---|---|
| Verapamil hydrochloride[1] | 6.67 | 0 |
| Natrosol[2] | 1.0 | 1.0 |
| Ethanol | 30 | 30 |
| Water[3] | to 100 | to 100 |

[1]ex Sigma
[2]Hydroxyethylcellulose, ex Hercules
[3]Compositions were titrated to pH 7.0 with 2M aqueous sodium hydroxide solution prior to being made up to 100% with distilled water.

The gel compositions indicated in Table 4 were applied to the shaved, bathed axillae of 9 female panellists. Two 1 cm$^2$ sites, in the same axilla of each panellist, were marked and 150 mg of the test composition was applied to one site and 150 mg of the control composition was applied to the other. Following application, the sites were covered with an occlusive patch for 6 hours. After this time, the occlusive patches were removed and, after a further hour, the panellists were required to sit in a hot room at 40° C. and 40% relative humidity for 80 minutes. During the latter 40 minutes of this period, sweat production from the 1 cm$^2$ sites was monitored using a micro-gravimetric technique. The sweat weight produced from the site treated with the test composition was found, on average, to be 28% less than that produced from the site treated with the control composition. This result was significant at the 99% level.

Examples 5 to 11

The following Tables illustrate cosmetic compositions comprising CCBAs that may be prepared and used in accord with the present invention. Amounts given in the Tables are percentages by weight.

TABLE 5

Aerosol Compositions

| Example: | 5.1 | 5.2 | 5.3 | 5.4 | 5.5 | 5.5 |
|---|---|---|---|---|---|---|
| CAP 40[1] | 92 | 85 | 35 | 84.96 | 85 | 35 |
| Ethanol (96%) | 0 | 0 | 62.17 | 0 | 0 | 61.16 |
| DC 245[2] | 6.2 | 6.9 | 0 | 6.4 | 6.5 | 0 |
| AACH[3] | 0 | 5 | 0 | 5 | 5 | 0 |
| CCBA | 1.0 | 2.0 | 1.0 | 1.0 | 1.0 | 1.0 |
| Bentone 38[4] | 0.6 | 0.5 | 0 | 0.5 | 0.5 | 0 |
| DTPA[5] | 0 | 0 | 0 | 1.0 | 0 | 0 |
| Cosmocil stearate[6] | 0 | 0 | 0 | 0.04 | 0 | 0 |
| Irgasan DP-300[7] | 0 | 0 | 0 | 0 | 0 | 0.01 |
| Ferulic acid[8] | 0 | 0 | 0 | 0 | 1.0 | 1.0 |
| Perfume | 0 | 0.6 | 1.5 | 1.0 | 1.0 | 1.5 |
| Isopropyl myristate | 0 | 0 | 0.33 | 0 | 0 | 0.33 |
| Propylene carbonate | 0.2 | 0 | 0 | 0 | 0 | 0 |

[1]Mixture of butane, isobutane and propane, ex Calor.
[2]Cyclomethicone, ex Dow Corning.
[3]Activated aluminium chlorohydrate, grade A296, ex Giulini.
[4]Quaternium-18 hectorite, ex Rheox.
[5]Diethylenetriaminepentaacetic acid, sieved to <63 $\mu$m.
[6]Polyhexamethylene biguanide salt, ex Zeneca.
[7]Triclosan, ex Ciba-Geigy.
[8]4-Hydroxy-3-methoxycinnamic acid, a deodorant active as disclosed in WO 00/01359 (Unilever).

TABLE 6

Aerosol Compositions

| Example: | 6.1 | 6.2 | 6.3 | 6.4 | 6.5 | 6.6 |
|---|---|---|---|---|---|---|
| Cyclomethicone (DC 245) | 3.47 | 11.8 | 14.4 | 3.55 | 4.1 | 5.2 |
| Ethanol | | | 20 | | | |
| Isopropyl palmitate | | | 10.3 | | 8.5 | |
| Isopropyl myristate | | | | | | 0.31 |
| PPG-14 butyl ether | 9.7 | 0.7 | | | | 9.1 |
| Octyldodecanol | | 0.25 | | | | |
| Polydecene | | | | | | 0.3 |
| Dibutyl phthalate | | | | | 4.5 | |
| Bentone 38 (ex Rheox) | 1 | 1 | 1.5 | 1 | 0.95 | 0.7 |
| Propylene carbonate | | | | | 0.15 | |
| Methylpropanolamine | | | | | | 0.08 |
| Silicone gum (Q2-1401) | | | | 0.2 | | |
| AACH | | | 10 | 4 | | |
| Milled AACH | 10 | | | | | 2 |
| Aluminium chlorohydrate | | | | 9.2 | 9.3 | |
| Silica | | 0.1 | | | | 0.01 |
| Talc | | | 3 | | | |
| Micronised polyethylene | | | | | 9.3 | |
| Perfume | 0.5 | 0.7 | 0.7 | 0.7 | | 1 |
| Allantoin | | | | | 1.5 | |
| Palmitoyl ethanolamide | 0.3 | 0.3 | 0.3 | 0.3 | 0.3 | 0.3 |
| CCBA | 0.03 | 0.15 | 0.6 | 0.25 | 1.4 | 1 |
| n-Pentane | | | | 20 | | |
| C3/C4 hydrocarbons | 75 | 75 | 40 | 70 | 60 | 80 |

TABLE 7

Lotion/Roll-on Compositions

| Example: | 7.1 | 7.2 | 7.3 | 7.4 | 7.5 | 7.6 | 7.7 | 7.7 | 7.9 |
|---|---|---|---|---|---|---|---|---|---|
| Ethanol | | 30 | | 60 | | | | 28 | |
| Isopropanol | 30 | | 30 | | 30 | 60 | 30 | | |
| Hydroxypropyl-cellulose | 0.7 | 0.7 | 0.7 | 0.7 | 0.7 | 0.7 | 0.7 | 0.7 | |
| Aluminium chlorohydrate | | 4 | 4 | | | | | 20 | |
| ZACH | | | | | | | 20 | | |
| AAZG | | | | | | | | | 18 |
| Cosmocil CQ | | | | 0.2 | 0.2 | | | | |
| Triclosan | | | | | | 0.1 | | | |
| Suspending Agent | | | | | | | | | 3 |
| Propylene Carbonate | | | | | | | | | 1 |
| Talc | | | | | | | | | 6 |
| CCBA | 0.2 | 0.4 | 0.6 | 0.8 | 1 | 2 | 3 | 4 | 5 |
| Water + minors | 69.1 | 64.9 | 64.7 | 38.3 | 68.1 | 37.2 | 46.3 | 47.3 | |
| DC 245 + minors | | | | | | | | | 67 |

TABLE 8

Cream and Soft Solid Compositions

| Example: | 8.1 | 8.2 | 8.3 | 8.4 | 8.5 |
|---|---|---|---|---|---|
| C18–C36 acid glycol ester | | 2.5 | | 3.75 | |
| Castor wax | | 7.5 | | 1.25 | |
| Triacontenyl vinyl pyrrolidone copolymer | 5 | | | | |
| Paraffin wax | 5 | | | | |
| Silica | | 1 | | | 0.2 |
| Cyclopentasiloxane and cetearyl-dimethicone/vinyl dimethicone co-polymer | | | | | 64.05 |
| C12–15 alkyl benzoate | 64.3 | 63.1 | 62.9 | 63.7 | 4 |
| Dextrin palmitate | | | 10 | 5 | |
| Neopentyl glycol diheptanoate | | | | | 5 |
| PEG-8 distearate | | | | | 2 |
| Stearyl dimethicone | | | | | 0.75 |
| AACH | 25 | | | 25.5 | |
| Milled AACH | | 25.5 | 26 | | |
| AAZG | | | | | 22 |
| CCBA | 0.2 | 0.4 | 0.6 | 0.8 | 1.5 |
| Perfume | 0.5 | | 0.5 | | 0.5 |

TABLE 9

Cream and Soft Solid Compositions

| Examples: | 9.1 | 9.2 | 9.3 | 9.4 | 9.5 | 9.6 | 9.7 | 9.8 |
|---|---|---|---|---|---|---|---|---|
| Silicone wax | 2.5 | | 3 | | | | | |
| N-lauroyl glutamic acid dibutylamide | | 1 | | | | | | |
| C18-C36 acid glycol ester | | | | 5 | | | | |
| C18-C36 acid triglyceride | | | | 1.25 | | | | |
| Castor wax | | | | | 4 | | | |
| Stearyl alcohol | | | | | 6 | | | |
| Paraffin wax | 7.5 | | | | | | | |
| Candelilla wax | | | | | | 7 | | |
| C24/28 alkyl dimethicone wax | | | | | | 3.5 | | |
| Silica | | | 1.5 | 1.5 | | | | |
| Talc | | 1.75 | | 6 | 5 | | | |
| Bentone 38 | | | 3 | | 0.5 | | | |
| Anhydrous aluminium silicate | | | 6 | | | | | |
| Microthene powder | | | | | | 6 | | |
| Propylene carbonate | | | | | | | 1.5 | |
| Cyclomethicone | 64.4 | | 61 | 62.5 | 36.3 | 56 | 43 | 47.8 |
| Tetraphenyl tetramethyl-siloxane | | 52.7 | | | | | | |
| C12-15 Alkyl benzoate | | | | 10 | | | | 11.7 |
| Dextrin palmitate | | 5 | | | | | | 9 |
| Octyldodecanol | | 15 | | | | | | |
| PPG14 butyl ether | | | | | | | 4.5 | |
| Dimethicone (10 mPa·s) | | | 5 | | 10 | | | |
| Dimethicone (350 mPa·s) | | | | | | | | 24 |
| POE-100 stearyl ether | | | | | | | 2 | |
| POE-100 stearate | | | | | | | 1 | |
| AACH | 25.5 | | | 22 | | | | |
| Milled AACH | | 25.5 | | | | | | |
| Aluminium chlorohydrate | | | | | | | | 18 |
| AAZG | | | 25 | | 25.7 | 20 | | 26.5 |
| CCBA | 0.1 | 0.3 | 0.5 | 1 | 2 | 3 | 4 | 5 |
| Perfume | | 0.5 | 0.5 | | | 0.5 | | |

TABLE 10

Solid Stick Compositions

| Examples: | 10.1 | 10.2 | 10.3 | 10.4 | 10.5 | 10.6 |
|---|---|---|---|---|---|---|
| Cyclomethicone (DC245) | 40.7 | 37.3 | 40.1 | 39.7 | 45.55 | |
| Permethyl 103A | 16 | 12 | | | | |
| PPG-14 Butyl ether | | | 4 | 10 | | |
| Propylene glycol | | | | | | 47.8 |

TABLE 10-continued

Solid Stick Compositions

| Examples: | 10.1 | 10.2 | 10.3 | 10.4 | 10.5 | 10.6 |
|---|---|---|---|---|---|---|
| Ethanol | | | | | | 13 |
| Isostearyl alcohol | | | | | | 12 |
| Stearyl alcohol | 14 | 14 | 17 | 11.5 | | |
| Castor wax | 2 | 5 | 2.5 | 5 | | |
| 12-hydroxystearic acid | | | | | 6 | |
| N-lauroyl glutamic acid dibutylamide | | | | | 2 | |
| Dibenzyilidene sorbitol | | | | | | 3 |
| Eicosanol | 0.2 | 0.2 | | | | |
| Octyldodecanol | | | | 14 | 14 | |
| C20–40 alcohols | | | | | 0.5 | |
| C20–40 pareth-3/C20–40 pareth-20 | | | | 1.75 | | |
| PEG-8 distearate | | | | 0.6 | 5 | |
| Amino-2-methyl-1-propanol | | | | | | 0.2 |
| ZAG | 23 | 25 | 24 | 26 | 26 | 22.5 |
| Glycerol | | | | 2 | | |
| EDTA | | | | 1 | | |
| Talc | 3 | | | | | |
| Fumed silica | | 1 | 2 | | | |
| Perfume | 1 | 1 | 1 | | | |
| CCBA | 0.1 | 0.5 | 0.8 | 1 | 1 | 1.5 |

TABLE 11

Solid Stick Compositions

| Examples: | 11.1 | 11.2 | 11.3 | 11.4 | 11.5 | 11.6 |
|---|---|---|---|---|---|---|
| Cyclomethicone (DC245) | 36.3 | 49.25 | 10 | 37 | | |
| Mineral oil | 11.5 | | | | | |
| Polydecene | | | 12.7 | | | |
| PPG-14 butyl ether | | | 2.5 | | | |
| C12–15 alkyl benzoate | | | | 15 | | |
| Dimethicone (50 mPa.s) | 1.5 | | | | | |
| Propylene glycol | | | | | 31 | 53.5 |
| Ethanol | | | | | 50 | |
| Water | | | | | 8.7 | 20 |
| Stearyl alcohol | 14 | | | | 1 | |
| Castor wax | 4.5 | | | | | |
| Dextrin palmitate | | 10 | | | | |
| Cellobiose octanonanoate | | | 3.8 | | | |
| Beta sitosterol | | | | 2.5 | | |
| Oryzanol | | | | 2.5 | | |
| Sodium stearate | | | | | 5.8 | 7.7 |
| Eicosanol | 0.2 | | | | | |
| Isopropyl myristate | | 10 | | | | |
| Cetyl dimethicone copolyol | | | 1 | 1 | | |
| Amino-2-methyl-1 propanol | | | | | | 0.5 |
| Poloxamer 407 | | | | | | 6 |
| Cocamide DEA | | | | | | 7 |
| Aluminium | 26 | 30 | | | | |

TABLE 11-continued

Solid Stick Compositions

| Examples: | 11.1 | 11.2 | 11.3 | 11.4 | 11.5 | 11.6 |
|---|---|---|---|---|---|---|
| chlorohydrate | | | | | | |
| Zirkonal 50 | | | 51.7 | 40 | | |
| Triclosan | | | | | | 0.3 |
| Glycerol | 2 | | 17.3 | | | |
| Talc | 1.5 | | | | | |
| Fumed silica | 1 | | | | | |
| Perfume | 1 | | | | | |
| CCBA | 0.5 | 0.75 | 1 | 2 | 3.5 | 5 |

What is claimed is:

1. A method of reducing perspiration or body malodour in the underarm areas comprising the topical administration of a cosmetic product comprising an effective amount of a calcium channel blocking agent having a molecular weight of less than 750.

2. A method according to claim 1 resulting in reduced body malodour.

3. A method of reducing perspiration or body malodour in the feet areas comprising the topical administration of a cosmetic product comprising an effective amount of a calcium channel blocking agent having a molecular weight of less than 750.

4. A method according to claim 1 wherein said calcium channel blocking agent is an L-type calcium channel blocking agent.

5. A method according to claim 1, wherein said calcium channel blocking agent is Safrole, tanshinone, magnolol, or denudin B.

6. A method according to claim 4, wherein said calcium channel blocking agent is verapamil (or a salt thereof) or methoxy-verapamil (or a salt thereof).

7. A method according to claim 1, wherein said calcium channel blocking agent is present in the cosmetic product at a level of from 0.1 to 250 mmol.kg$^{-1}$.

8. A method according to claim 1, wherein a skin penetration enhancer is used to aid the transport of the calcium channel blocking agent from the skin surface to the secretory coil cells of the sweat glands.

9. A method according to claim 1, wherein iontophoresis is used to aid the transport of the calcium channel blocking agent from the skin surface to the secretory coil cells of the sweat glands.

10. A cosmetic method of reducing underarm perspiration according to claim 1, said method comprising topical application of a cosmetic product comprising an effective amount of a calcium channel blocking agent having a molecular weight of less than 750 to the underarm area.

* * * * *